(12) United States Patent
Moser et al.

(10) Patent No.: US 9,180,128 B2
(45) Date of Patent: Nov. 10, 2015

(54) STABLE PHARMACEUTICAL COMPOSITIONS OF 5,10-METHYLENE TETRAHYDROFOLATE

(75) Inventors: Rudolf Moser, Schaffhausen (CH); Thomas Ammann, Marthalen (CH)

(73) Assignee: MERCK & CIE, Schaffhausen (CH)

( * ) Notice: Subject to any disclaimer, the term of this patent is extended or adjusted under 35 U.S.C. 154(b) by 1892 days.

(21) Appl. No.: 10/562,200

(22) PCT Filed: Jun. 28, 2004

(86) PCT No.: PCT/EP2004/006944
§ 371 (c)(1),
(2), (4) Date: Nov. 8, 2006

(87) PCT Pub. No.: WO2004/112761
PCT Pub. Date: Dec. 29, 2004

(65) Prior Publication Data
US 2007/0099866 A1    May 3, 2007

(30) Foreign Application Priority Data
Jun. 26, 2003  (CH) .............................. 2003 1123/03

(51) Int. Cl.
*A61K 31/519* (2006.01)
*A61K 31/00* (2006.01)
*A61K 31/191* (2006.01)

(52) U.S. Cl.
CPC ............... *A61K 31/519* (2013.01); *A61K 31/00* (2013.01); *A61K 31/191* (2013.01)

(58) Field of Classification Search
CPC .................................................... A61K 31/519
See application file for complete search history.

(56) References Cited

U.S. PATENT DOCUMENTS

| 4,931,441 A | 6/1990 | Lawrence |
| 5,434,087 A | 7/1995 | Beggs et al. |
| 5,989,566 A * | 11/1999 | Cobb et al. ................. 424/278.1 |
| 5,997,915 A | 12/1999 | Bailey et al. |
| 6,613,767 B1 | 9/2003 | Nijkerk et al. |
| 2002/0052374 A1* | 5/2002 | Rabelink et al. ............... 514/250 |
| 2002/0183277 A1* | 12/2002 | Binderup ........................ 514/50 |

FOREIGN PATENT DOCUMENTS

| WO | WO 95/26963 A | 10/1995 |
| WO | WO 97/27764 A | 8/1997 |

OTHER PUBLICATIONS

Odin Elisabeth et al., Chemical Stability and Human Plasma Pharmacokinetics of Reduced Folates, Cancer Investigation, 1998, pp. 447-455, vol. 16, No. 7.

* cited by examiner

*Primary Examiner* — Paul Zarek
(74) *Attorney, Agent, or Firm* — Millen White Zelano & Branigan, P.C.

(57) ABSTRACT

This invention relates to stable pharmaceutical compositions of 5,10-methylene-(6R)-, -(6S)- or -(6R,S)-tetrahydrofolate (MTHF), by adjusting to a basic pH and the simultaneous use of citrate. Stabilisation is effected even in the absence of a reducing agent. The present invention is particularly suitable for producing lyophilisation solutions and lyophilisates or dry powders and dry mixtures, since the stable MTHF solutions can be used in high concentrations for filling corresponding vessels such as vials, ampoules, etc. The lyophilisates have a surprisingly long shelf life and are surprisingly stable. They can be reconstituted without problems by adding water or aqueous solutions, and the final clear injection solutions again exhibit excellent stability properties. Moreover, the present invention even makes it possible to prepare difficultly soluble calcium 15 or acidic salts of MTHF in high concentrations and as physiologically compatible isotonic solutions.

25 Claims, No Drawings

STABLE PHARMACEUTICAL COMPOSITIONS OF 5,10-METHYLENE TETRAHYDROFOLATE

This invention relates to stable pharmaceutical compositions of 5,10-methylene-(6R)-, -(6S)- or -(6R,S)-tetrahydrofolate.

In the present text, the term 5,10-methylenetetrahydrofolate (abbreviated to MTHF) relates to 5,10-methylenetetrahydrofolic acid and polyglutamates thereof in the form of the free acids, in the form of pharmaceutically acceptable salts, particularly acidic salts, as well as alkali or alkaline earth metal salts. 5,10-methylenetetrahydrofolic acids and polyglutamates thereof comprise both mixtures of optical isomers, particularly 1:1 mixtures of diastereoisomers, as well as optically pure diastereoisomers, particularly optically pure, natural 5,10-methylene-(6R)-tetrahydrofolic acid.

Pharmaceutically acceptable salts can be acidic salts, such as sulphate or sulphonate salts, preferably sulphate salts, or can also be alkali or alkaline earth metal salts, preferably sodium, potassium, magnesium or calcium salts.

MTHF is an active ingredient which is preferably used for parenteral administration in combination with fluorinated pyrimidines, such as 5-fluorouracil (5-FU), which is a widely used cytostatic agent for the treatment of solid tumours [Cofactor Biokeys Pharmaceuticals. Seley, K. L. Idrugs 4 (1), 99-101 (2001)]. MTHF is a reduced folate and achieves its chemotherapeutic effect together with the base analogue 5-FdUMP by inhibiting the enzyme thymidylate synthase (TS), which catalyses the conversion of deoxyuridylate (dUMP) to deoxythymidylate (dTMP), which is a central component of DNA synthesis. Since this step constitutes the only de novo source of deoxythymidylate in the cell, the inhibition of this key enzyme by pyrimidine bases such as 5-FU or the 5-FU prodrug capecitabine (Xeloda) is one of the main starting points in cancer therapy. Deactivation of TS occurs by the formation of a covalent, inhibiting ternary complex between TS, the base analogue 5-FdUMP, which is a metabolite of 5-FU, and MTHF. An enhancement of the cytotoxic effect of 5-FU can be achieved by increasing the intracellular concentration of MTHF, whereupon the stability of the ternary complex is increased. This causes direct inhibition of DNA synthesis and repair, which ultimately results in cell death and in the delaying of tumour growth.

The pharmaceutical use of MTHF is restricted by its extremely high sensitivity to oxidation by air [Chemical Stability and Human Plasma Pharmacokinetics of Reduced Folates. Odin, E. et al., Cancer Investigation 16 (7), 447-455 (1998). The structure of "Active Formaldehyde" ($N^5N^{10}$-methylene tetrahydrofolic acid), Osborn, M. J. et al., J. Am. Chem. Soc. 82, 4921-4927 (1960), Folates in Foods: Reactivity, stability during processing, and nutritional implications. Hawkes, J., and Villota, R. Food Sci. Nutr. 28, 439-538 (1989)]. MTHF is an addition product of tetrahydrofolic acid (THF) and formaldehyde [5,10-methylene-5,6,7,8-tetrahydrofolate]. Conformation of the Tetrahydropyrazine and Imidazolidine Rings. Poe, M. et al. Biochemistry 18 (24), 5527-5530 (1979). Tetrahydrofolic Acid and Formaldehyde. Kallen, R. G. Methods in Enzymology 18B, 705-716 (1971)]. In aqueous solution there is an equilibrium between MTHF on the one hand and THF and formaldehyde on the other hand. The following procedures have hitherto been employed for the stabilization of MTHF solutions:

Rigorous exclusion of atmospheric oxygen by the use of special technical devices for the reconstitution of solid formulations and the injection of MTHF in an air-free environment [Chemical Stability and Human Plasma Pharmacokinetics of Reduced Folates. Odin, E. et al., Cancer Investigation 16 (7), 447-455 (1998), Fluid Transfer Systems U.S. Pat. No. 4,564,054].

Addition of a reducing agent such as L(+)-ascorbic acid or salts thereof, reduced γ-glutathione, β-mercaptoethanol, thioglycerol, N-acetyl-L-cysteine, etc. as an antioxidant for the sensitive MTHF and for THF in particular.

Stabilization by means of cyclodextrin inclusion compounds: EP 0 579 996 (Eprova). Use of high concentrations of the active ingredient.

The following methods are also known for the stabilization of other tetrahydrofolic acid derivatives:

Stabilization of solutions containing 5-formyltetrahydrofolic acid by the addition of sodium citrate, sodium acetate or sodium chloride: EP 0 755 396 (Pharmachemie).

Stabilization of injection solutions containing a sodium or potassium salt of 5-formyltetrahydrofolic acid at a pH between 7.5 and 8.5: EP 0 677 159 (SAPEC).

Stabilization of solutions containing the calcium salt of 5-formyltetrahydrofolic acid by the addition of sodium citrate: U.S. Pat. No. 4,931,441 (Luitpold Pharmaceutical).

However, the stabilization of 5-formyltetrahydrofolic acid, particularly solutions thereof, cannot be compared with the stabilization of 5,10-methylenetetrahydrofolic acid solutions. Thus the methylene group in 5,10-methylenetetrahydrofolic acid, which is incorporated in a five-membered ring, results in properties of this substance which differ considerably from those of 5-formyltetrahydrofolic acid. This is manifested, for example, in significantly different stability behaviour and in different paths of decomposition. In contrast to 5-formyltetrahydrofolic acid, 5,10-methylenetetrahydrofolic acid in solution is always in equilibrium with formaldehyde and tetrahydrofolic acid (THF), which is distinguished by its extremely high sensitivity to oxidation. In contrast, 5-formyltetrahydrofolic acid does not exhibit this dissociation behaviour and is generally very stable in pharmaceutically acceptable aqueous solutions, even without the addition of sodium citrate and sodium hydroxide.

Therefore, no stable pharmaceutical compositions of MTHF have hitherto been described.

It has now surprisingly been found that the stability of MTHF in aqueous solutions, in suspensions and in solid forms such as powders or lyophilisates can be strikingly increased by adjusting to a basic pH, with the simultaneous use of citrate. Surprisingly, this stabilization occurs even in the absence of a reducing agent.

Thus, even without additions of reducing agents (antioxidants) and without the exclusion of atmospheric oxygen, MTHF solutions are stable for hours. This is all the more surprising since stable compositions of MTHF cannot be obtained using acetate, oxalate, maleate and salts of other acids instead of citrate. This is also in contrast to the situation for 5-formyltetrahydrofolic acid, where an effect comparable with that of citrate can be obtained with acetate (EP 0 755 396). In 5-formyltetrahydrofolic acid solutions citrate reduces hydrolysis and oxidative cleavage of the basic skeleton and thus reduces the formation of products such as p-aminobenzoylglutamic acid and pterin- and tetrahydropterin derivatives.

In contrast to this, for MTHF in the basic pH region citrate inhibits the separation of formaldehyde (hydrolysis) from the molecule. This is a striking and surprising difference in the behaviour of these two compounds, both of which form part of the folate class of substances.

Furthermore, the present invention even makes it possible to prepare difficultly soluble calcium or acidic salts [Eprova Patent: Stable salts of 5,10-methylenetetrahydrofolic acid—

EP 0 537 492] of MTHF in high concentrations and in physiologically acceptable isotonic solutions.

The unexpected stabilization of MTHF with citrate at basic pH values is due to a surprising synergistic effect of the citrate buffer solution in this pH range. Complex formation between citrate and MTHF on the one hand and between citrate and the counterion (salt) of MTHF on the other hand makes a decisive contribution to the stabilization of the methylene group by inhibiting the separation of formaldehyde (hydrolysis) from the MTHF molecule. The formation of THF, which is extremely sensitive to oxidation, is thereby prevented, as is the decomposition of MTHF.

In the compositions according to the invention, the pH is set within the range from 7.5-10.5, preferably 8.5-9.5. This effected with the aid of aqueous sodium hydroxide and hydrochloric acid in the MTHF solution, which contain citric acid, sodium dihydrogen citrate or tri-sodium citrate dihydrate as stabilization and buffer substances. It is also possible to add reducing agents, such as L(+)-ascorbic acid or salts thereof, reduced γ-glutathione, β-mercaptoethanol, thioglycerol, N-acetyl-L-cysteine, etc. as antioxidants.

The formulations according to the invention are also particularly suitable for producing lyophilisation solutions and lyophilisates or dry powders and dry mixtures, since the stable MTHF solutions can be used in high concentrations for filling corresponding vessels, e.g. vials, ampoules, etc.. The lyophilisates can be stored surprisingly well, and are surprisingly stable. They can be reconstituted without problems by the addition of water or aqueous solutions, and the final clear injection solutions again exhibit excellent stability properties.

The claimed formulations are preferably used for parenteral administration. However, formulations are also produced for enteral (e.g. oral, sublingual or rectal) administration or for topical (e.g. transdermal) application.

The formulations are preferably used directly as water-based solutions or oil-based suspensions, or as lyophilisates. Preparations for parenteral application comprise sterile, aqueous and nonaqueous injection solutions and suspensions of the active compounds which preferably comprise an isotonic composition.

The formulations can also be administered with a carrier, however. Suitable carriers include organic or inorganic substances which do not react with the active ingredient, e.g. oil, benzyl alcohol, polyethylene glycol, glycerol triacetate or other fatty acid glycerides, gelatine, lecithin, cyclodextrins, carbohydrates such as lactobiose or starch, magnesium stearate, talc or cellulose. Tablets, dragees, capsules, powders, syrups, concentrates or drops are preferred for oral application, and suppositories are preferred for rectal application.

Suspensions, emulsions or implants can also be used, and patches or creams can be used for topical application.

The preparations can comprise stabilisers, additives for the controlled release of pharmaceutically active compounds, antioxidants, buffers, bacteriostatic agents and adjuvants for obtaining an isotonic solution. Aqueous and non-aqueous sterile suspensions can contain suspension additives and thickeners. The preparation can exist as a single-dose or as a multiple-dose container, e.g. as welded ampoules or vials with a stopper and a closure cap. They can be stored as a freeze-dried product and when required can be prepared for use by adding a sterile liquid, e.g. water or a physiological salt solution. Sterile powders, granules or tablets can also be used in this manner.

All preparations can additionally contain one or more separately or synergistically acting active compounds. In particular, these include fluorinated pyrimidine bases such as 5-fluorouracil (5-FU), capecitabine (Xeloda), tegafur, UFT, doxifluridine, 2'-deoxy-5-fluorouridine, various cytostatic agents such as gemcitabine (Gemzar), docetaxel (Taxotere), paclitaxel (Taxol), topotecan (Hycamtin), irinotecan (CPT-11), doxorubicin (Rubex), mitomycin (MTC), cisplatin (CDDP), cyclophosphamide (CPM), methotrexate (Amethopterin), pemetrexed (Alimta), vincristine (VCR), cytarabine (Ara-C), epirubicin (Ellence), oxaliplatin (Eloxatin), tamoxifen (Nolvadex), carboplatin (CBDCA), etoposide (Etopophos), ifosfamide (Ifex) or antioxidants such as vitamin C, vitamin E, glutathione, thioglycerol and acetylcysteine, as well as the two MTHF dissociation products formaldehyde and tetrahydrofolic acid.

The preparation comprises between 0.001 mg and 10,000 mg MTHF per dose. Preparations which preferably contain between 1 mg and 1,000 mg MTHF per dose are used in therapy.

The dosage depends on the form of therapy, on the form of application of the preparation, and on the age, weight, nutrition and condition of the patient. Treatment can commence with a smaller amount, below the optimum amount, which can be increased in order to achieve the optimum effect. The preferred dose used in therapy ranges between 1 mg and 1,000 mg per day, particularly between 100 mg and 500 mg per day. Administration can be effected either as a single dose or as a repeated dose.

The preparations can be used in all fields of application for folates.

From the preceding description, one skilled in the art in this field can read the crucial elements of the invention without problems, and, without departing from the basic idea and from the scope of the invention, can make modifications and additions and can thereby adapt the invention to differing needs and conditions.

The entire disclosures of all the patent applications, patents and publications which are cited in this text are included jointly by reference.

The following examples can be carried out with a similar degree of success by replacing the generic or specifically described products and/or process conditions by those which are given in the following examples. The following specific embodiments are likewise purely exemplary and should by no means be considered as having a limiting effect on the remainder of the disclosure.

EXAMPLES TO ILLUSTRATE THE INVENTION

Example 1

A lyophilisate containing
5,10-methylene-(6R,S)-tetrahydrofolic acid 9900 ml water were saturated with argon. 421.9 g citric acid were completely dissolved therein with stirring. 232.0 g 5,10-methylene-(6R,S)-tetrahydrofolic acid, calcium salt were added. The pH was adjusted to 8.0 with aqueous sodium hydroxide, whereupon the 5,10-methylene-(6R,S)-tetrahydrofolic acid was slowly dissolved. Thereafter, the pH was adjusted to 8.5 with aqueous sodium hydroxide. The solution was filtered under sterile conditions and was introduced at 5.0 ml per vial into 10 ml glass vials. Thereafter, the solution was frozen and freeze-dried.

Vials were obtained which contained 5,10-methylene-(6R,S)-tetrahydrofolic acid.

Example 2

Stabilization of 5,10-methylene-(6R,S)-tetrahydrofolic acid (lyophilisate)

Vials produced as in Example 1 exhibited the following stability values (Am 1466-A):

| Storage at +4° C (% relative stability) Duration (months) | | | | | | | |
|---|---|---|---|---|---|---|---|
| 0 | 3.0 | 6.0 | 9.0 | 12.0 | 18.0 | 24.0 | 36.0 |
| 100.0 | 100.4 | 99.3 | 98.5 | 99.0 | 99.4 | 98.0 | |

| Storage at −15° C (% relative stability) Duration (months) | | | | | | | |
|---|---|---|---|---|---|---|---|
| 0 | 3.0 | 6.0 | 9.0 | 12.0 | 18.0 | 24.0 | 36.0 |
| 100.0 | 99.8 | 97.9 | 98.3 | 98.8 | 98.8 | 98.4 | |

Compared with this, the untreated reference sample of the calcium salt of 5,10-methylene-(6R)-tetrahydrofolic acid exhibited the following stability values (Co 751):

| Storage at +25° C (% relative stability) Duration (months) | | | | | | | |
|---|---|---|---|---|---|---|---|
| 0 | 0.5 | 1.0 | 1.75 | 2.5 | 4.5 | 9.2 | 19.0 |
| 100.0 | 92.3 | 83.4 | 77.2 | 71.9 | 61.5 | 49.1 | 43.0 |

Example 3

Stabilization of 5,10-methylene-(6R,S)-tetrahydrofolic acid (solutions)

Compositions prepared as in Example 1 exhibited the following stability values as a dilute solution in physiological common salt solution (AC0448):

| Storage at +25° C (% relative stability) without the exclusion of air Duration (hours) | | | | | | | |
|---|---|---|---|---|---|---|---|
| 0 | 0.67 | 1.33 | 2.0 | 2.67 | 3.33 | 4.0 | 32.2 |
| 100.0 | 97.6 | 95.1 | 94.6 | 93.7 | 92.1 | 89.9 | 51.8 |

Compositions prepared as in Example 1 exhibited the following stability values as a dilute aqueous solution (AC0447):

| Storage at +25° C (% relative stability) without the exclusion of air Duration (hours) | | | | | | | |
|---|---|---|---|---|---|---|---|
| 0 | 0.67 | 1.33 | 2.0 | 2.67 | 3.33 | 4.0 | 32.2 |
| 100.0 | 97.7 | 97.0 | 96.6 | 94.8 | 93.8 | 93.3 | 70.9 |

Compositions prepared as in Example 1 exhibited the following stability values as a concentrated aqueous solution (AC0447):

| Storage at +25° C (% relative stability) without the exclusion of air Duration (hours) | | | | | |
|---|---|---|---|---|---|
| 0 | 2.0 | 4.0 | 6.0 | 12.0 | 24.0 |
| 100.0 | 100.2 | 99.2 | 98.1 | 95.9 | 86.2 |

As a comparison with the above, the following stability values are given in the prior art for the calcium salt of 5,10-methylene-(6R,S)-tetrahydrofolic acid in physiological common salt solution [see Chemical Stability and Human Plasma Pharmacokinetics of Reduced Folates. Odin, E. et al. Cancer Investigation 16 (7), 447-455 (1998)].

| Storage at +25° C (% relative stability) | | | | | |
|---|---|---|---|---|---|
| | | Duration (hours) | | | |
| | 0 | 4.0 | 24.0 | 26.0 | 48.0 |
| With the exclusion of air | 100.0 | 58.0 | 38.0 | 18.0 | 8.0 |
| Without the exclusion of air | 100.0 | 84 | 12.0 | 8.0 | 6.0 |

Example 4

Tablet containing 5,10-methylene-(6R)-tetrahydrofolic acid 990 l water were saturated with argon. 42.2 kg citric acid were completely dissolved therein with stirring. 21.4 kg 5,10-methylene-(6R)-tetrahydrofolic acid were added as the free acid. The pH was adjusted to 8.0 with aqueous sodium hydroxide, whereupon the 5,10-methylene-(6R)-tetrahydrofolic acid was slowly dissolved. Thereafter, the pH was adjusted to 8.5 with aqueous sodium hydroxide. The solution was filtered under sterile conditions and lyophilised. An amount of the lyophilisate containing 1,000 g 5,10-methylene-(6R)-tetrahydrofolic acid was pressed into tablets with 4 kg lactose, 1.2 kg starch, 0.2 kg talc and 0.1 kg magnesium stearate so that each tablet contained 100 mg 5,10-methylene-(6R)-tetrahydrofolic acid.

The tablet can also be coated as a film tablet.

Example 5

Suppositories containing 5-methylene-(6R,S)-tetrahydrofolic acid

A lyophilisate prepared as in Example 1 and containing 500 g 5,10-methylene-(6R,S)-tetrahydrofolic acid was melted with 50 g hydroxypropylcellulose and 2 kg of semi-synthetic glycerides to form suppositories so that each suppository contained 500 mg 5,10-methylene-(6R,S)-tetrahydrofolic acid.

Example 6

A combination preparation containing 5,10-methylene-(6R,S)-tetrahydrofolic acid and 5-fluorouracil, amongst other ingredients A combination preparation was produced, similarly to Examples 1, 4, 5 and 7, which in addition to the usual amount of 5,10-methylene-(6R,S)-tetrahydrofolic acid for the corresponding application also contained the usual amount of 5-fluorouracil for this application.

Example 7

A lyophilisate containing
5,10-methylene-(6R)-tetrahydrofolic acid 9900 ml water were saturated with argon. 316.5 g citric acid were completely dissolved therein with stirring. 212.5 g 5,10-methylene-(6R)-tetrahydrofolic acid sulphate were added. The pH was adjusted to 8.0 with aqueous sodium hydroxide, whereupon the 5,10-methylene-(6R)-tetrahydrofolic acid was slowly dissolved. Thereafter, the pH was adjusted to 8.5 with aqueous sodium hydroxide. The solution was filtered under sterile conditions and 5.0 ml per phial was introduced into 10 ml glass vials. Thereafter, the solution was frozen and freeze-dried.

Vials were obtained which contained 5,10-methylene-(6R)-tetrahydrofolic acid.

Example 8

Stabilization of 5,10-methylene-(6R)-tetrahydrofolic acid (solution)

Compositions prepared as in Example 7 exhibited the following stability values as a concentrated aqueous solution (Am 1758-2/a);

| Storage at +25° C (% relative stability), without the exclusion of air Duration (hours) | | | | | |
|---|---|---|---|---|---|
| 0 | 0.67 | 1.33 | 2.67 | 4.0 | 5.33 |
| 100.0 | 100.2 | 99.1 | 99.2 | 98.4 | 97.7 |

As a comparison with the above, the following stability values are given in the prior art for the calcium salt of 5,10-methylene-(6R,S)-tetrahydrofolic acid in physiological common salt solution [see Chemical Stability and Human Plasma Pharmacokinetics of Reduced Folates. Odin, E. et al. Cancer Investigation 16 (7), 447-455 (1998)].

| | Storage at +25° C (% relative stability) | | | | |
|---|---|---|---|---|---|
| | Duration (hours) | | | | |
| | 0 | 4.0 | 24.0 | 26.0 | 48.0 |
| With the exclusion of air | 100.0 | 58.0 | 38.0 | 18.0 | 8.0 |
| Without the exclusion of air | 100.0 | 84 | 12.0 | 8.0 | 6.0 |

The invention claimed is:

1. A stable pharmaceutical composition of 5,10-methylene-(6R)-, -(6S)-or -(6R,S)-tetrahydrofolate, comprising 5,10-methylene-(6R)-, -(6S) -or -(6R,S)-tetrahydrofolic acid or a pharmaceutically acceptable salt of 5,10-methylene-(6R)-, -(6S)-or -(6R,S)-tetrahydrofolic acid and citrate, and has a pH of 7.5 to 10.5.

2. A stable pharmaceutical composition according to claim 1, further comprising an additional pharmaceutically acceptable active ingredient or an adjuvant.

3. A pharmaceutical composition according to claim 2, wherein the adjuvant is formaldehyde.

4. A pharmaceutical composition according to claim 2, wherein the additional active ingredient is folate.

5. A pharmaceutical composition according to claim 4, wherein the folate is tetrahydrofolic acid or a salt thereof.

6. A pharmaceutical composition according to claim 1, wherein the pharmaceutically acceptable salt of 5,10-methylene-(6R)-, -(6S)-or -(6R,S)-tetrahydrofolic acid is a calcium or an acidic salt thereof.

7. A pharmaceutical composition according to claim 2, wherein the additional active ingredient is a cytostatic agent.

8. A pharmaceutical composition according to claim 2, wherein the additional active ingredient is a fluorinated pyrimidine compound.

9. A pharmaceutical composition according to claim 8, wherein the fluorinated pyrimidine compound is a 5-fluorouracil or a 5-fluoruracil compound.

10. A pharmaceutical composition according to claim 1, additionally comprising at least one antioxidant or a radical scavenger.

11. A pharmaceutical composition according to claim 10, wherein the antioxidant or radical scavenger is vitamin C or reduced glutathione.

12. A pharmaceutical composition according to claim 1, which is in the form of a lyophilisate, dry powder or dry mixture.

13. A pharmaceutical composition according to claim 1, which is in the form of a lyophilisation solution.

14. A method of stabilizing a composition comprising 5,10-methylene-(6R)-, -(6S)-or -(6R,S)-tetrahydrofolate according to claim 1, comprising treating 5,10-methylene-(6R)-, -(6S)-or -(6R,S)-tetrahydrofolic acid with citrate and bringing it to a pH of 7.5 to 10.5.

15. A method of preparing a composition according to claim 1 comprising bringing together a pharmaceutically acceptable salt of 5,10-methylene-(6R)-, -(6S)-or -(6R,S)-tetrahydrofolic acid and citrate at a pH of 7.5 to 10.5.

16. A pharmaceutical composition according to claim 1, which has a pH of 8.5 to 9.5.

17. A pharmaceutical composition according to claim 8, wherein the fluorinated pyrimidine compound is a capecitabine (xeloda).

18. A method for treating a solid tumor, comprising administering to a patient in need thereof an effective amount of a pharmaceutical composition according to claim 1.

19. A pharmaceutical composition according to claim 1, which has a pH of greater than 8.5 to up to 9.5.

20. A pharmaceutical composition according to claim 1, which is in the form of a lyophilisate.

21. A stable pharmaceutical composition of 5,10-methylene-(6R)-, -(6S)-or -(6R,S)-tetrahydrofolate, comprising 5,10-methylene-(6R)-, -(6S) -or -(6R,S)-tetrahydrofolic acid or a pharmaceutically acceptable salt of 5,10-methylene-(6R)-, -(6S)-or -(6R,S)-tetrahydrofolic acid and citrate, and has a pH of 7.5 to 10.5, which stable pharmaceutical composition is present without the exclusion of atmospheric oxygen.

22. A pharmaceutical composition according to claim 21, which does not contain a reducing agent.

23. A method according to claim 15, which is performed without the exclusion of atmospheric oxygen.

24. A method according to claim 15, which is performed without the addition of a reducing agent to the composition.

25. A pharmaceutical composition according to claim 20, which is in the form of a tablet that contains 100 mg to 500 mg of 5,10-methylene-(6R)-, -(6S)-or -(6R,S)-tetrahydrofolic acid.

* * * * *